United States Patent [19]

Scandurra et al.

[11] Patent Number: 5,314,689
[45] Date of Patent: May 24, 1994

[54] ACYL-CARNITINE FOR THE TREATMENT AND PREVENTION OF VIRAL INFECTIONS

[75] Inventors: Laura Scandurra, Catania, Italy; Laure Aurelian, Baltimore, Md.

[73] Assignee: Attilio Bernardini, Switzerland

[21] Appl. No.: 459,785

[22] PCT Filed: May 25, 1989

[86] PCT No.: PCT/CH89/00097
  § 371 Date: Mar. 21, 1990
  § 102(e) Date: Mar. 21, 1990

[87] PCT Pub. No.: WO89/11276
  PCT Pub. Date: Nov. 30, 1989

[30] Foreign Application Priority Data

May 26, 1988 [CH] Switzerland ............... 1984/88

[51] Int. Cl.$^5$ .............................................. A61F 13/00
[52] U.S. Cl. ................................. 424/433; 424/430; 424/436; 514/556; 514/931; 514/934; 514/967; 514/969
[58] Field of Search ............... 424/436; 514/556, 969, 514/967, 931, 934, 957

[56] References Cited

U.S. PATENT DOCUMENTS

| | | | |
|---|---|---|---|
| 4,107,328 | 8/1978 | Michaels | 514/556 |
| 4,194,006 | 3/1980 | Cavazza | 424/311 |
| 4,415,588 | 11/1983 | Cavazza | 424/311 |
| 4,790,978 | 12/1988 | Allenmark | 514/556 |
| 4,839,159 | 6/1989 | Winter | 514/556 |

FOREIGN PATENT DOCUMENTS

0126420 8/1982 Japan.

OTHER PUBLICATIONS

R. J. Gilbert et al., "Bromoacetyl-L-Carnitine: Biochemical and Antitrypanosomal Actions Against Trypanosoma Brucei Brucei," Biochemical Pharmacology, 22, pp. 3447-3451 (1983).
T. Nakadate et al., "Inhibition of 12-O-Tetradecanoyl-phorbol-13-acetate-induced Tumor Promotion and Epidermal Ornitbine Decarboxylase Activity in Mouse Skin by Palmitoylcarnitine," Cancer Research, 44, 1583-1593 (1986).
B. M. Patten et al., "Hepatitis-Associated Lipid Storage Myopathy," Annals of Internal Medicine, 87, pp. 417-421 (1977).
C. De Simone et al., "Amelioration of the Depression of HIV-Infected Subjects With L-Acetyl Carnitine Therapy," J. Drug Dev., 1, pp.163-166 (1988).

*Primary Examiner*—Gabrielle Phelan
*Attorney, Agent, or Firm*—Webb Ziesenheim Bruening Logsdon Orkin & Hanson

[57] ABSTRACT

Acyl-Carnitine in pharmaceutical formulations provides therapeutic and preventive antiviral action against HSV, CMV, VZV, HIV and others.

4 Claims, No Drawings

ACYL-CARNITINE FOR THE TREATMENT AND PREVENTION OF VIRAL INFECTIONS

Viruses of the most divergent type present a major health hazard for humans, animals and plants and can result in harmless to highly dangerous infections. In contrast to bacteria, viruses require a living host cell for life, development of their activity and for propagation.

A disquieting increase in sexually transmitted viral infections, such as those involving Herpes simplex virus (HSV), types 1 and 2, Cytomegalo virus (CMV), human immune deficiency virus (HIV), human papilloma virus (HPV), etc., has recently occurred with the changes in sexual mores.

At the present time, no satisfactory wide-ranging antiviral drug is available, with the exception of acycloguanosine (ACYCLOVIR), which is used in the treatment of Herpes, and azidothymidine (AZT), which is used in the treatment of AIDS.

None of these drugs is problem-free. In principle, however, preventive modalities are not obtainable.

Prevention is particularly desirable in cases involving HSV, CMV, HIV and VCV, in which the virus persists during the lifetime of the host and frequently causes illness many years later and with different pathologies.

All the remedies proposed to date were directed toward a direct combatting of the virus after its entrance into the cell, in order to inactivate or kill it there.

Surprisingly, a remedy was now developed that acts not only directly on virus replication, but also completely inactivates the virus by means of a still unexplained change in the host cell and makes virus survival impossible.

The remedy according to the invention is defined in patent claim 1, while particular embodiments can be deduced from the subordinate claims.

The preferred compound, which was found to be active in this connection, is L-acetyl-carnitine γ-trimethyl-β-acetyl-butyrobetaine) with the formula:

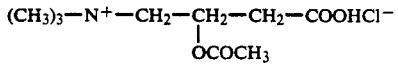

Carnitine is a compound that occurs naturally in the body. The ortho-L-acetyl derivative is also a known one, occurring both in various organs and also commercially available in synthetic form; it is recommended for example for peroral use in the form of pills or drops for the treatment of age-induced neurological metabolic disorders. For example, such disturbances are memory loss, strange behavior and erratic manifestations, such as are commonly known as dementia senilis. The recommended dosage is 30 mg/kg/day.

It has now been found in a completely unexpected manner that L-acetyl-carnitine has a potent antiviral activity and can be used for treating viral infections, but also in particular for the prevention of such infections with surprising success.

The studies conducted to demonstrate the antiviral activity of L-acetyl-carnitine can be summarized as follows:

1. Effect of L-acetyl-carnitine on viral growth in tissue cultures

Two trial series were conducted. In the first series, various cell lines of animal and human origin (African green monkey; human cervical cancer cells) were infected with various viruses, including HSV, types 1 and 2, CMV, Adenovirus, Varicella-Zoster virus (VZV), respiratory syncytial virus (RSV), polio virus, Coxsackie virus, enterovirus and vaccinia virus.

Five cultures of each, which were infected with the above viruses, were treated with 100 mg/ml of L-acetyl-carnitine.HCl or control medium (no active substance).

The virus titers were determined at daily intervals for 12 days.

All the controls reacted positively to the viral growth with titers in the range between $10^4$ and $10^8$ colony-forming units (plaque forming units pfu) /ml, depending on the specific virus.

On the other hand, all the specimens treated with L-acetyl-carnitine.HCl were negative (0 pfu/ml), i.e., no viral propagation occurred.

In the second trial series, the action of the L-acetyl-carnitine dosage on the antiviral activity was determined.

Five cultures of each were infected and treated with 10, 20, 30, 40, 50, 60, 70, 80, 90, 100, 200 and 400 mg/ml of L-acetyl-carnitine.HCl or a control medium and the virus titers were determined as above.

The antiviral activity was observed in all dosages of more than 10–20 mg/ml. The antiviral activity was manifested either completely or not at all and presented no dose-dependent pattern.

2. Effect of time of exposure in the antiviral activity

These trials were to determine the time during which an infection with HSV1 or HSV2 is prevented by L-acetyl-carnitine.

Five cultures each of infected cells were treated (40 mg/ml) at the following times: −24 hours, −12 hours, −2 hours, −1 hour, −30 minutes, −20 minutes, −10 minutes, 0, 1 hour, 2 hours, 3 hours, 4 hours, 8 hours, 12 hours and 16 hours after the infection.

They were examined for viral growth 24 hours after the infection.

Viral replication was completely suppressed in all cultures that had been treated between 24 hours before to 4 hours after the infection.

The viruses propagated normally in the cultures that had been treated with L-acetyl-carnitine later than 4 hours after the infection.

The prevention of viral growth was absolute (0 pfu/ml) in these studies, while the viruses propagated normally in the controls that were not treated with L-acetyl-carnitine or received this treatment more than 4 hours after the infection.

3. Minimum time of exposure required for the antiviral activity

Five cultures of each were subjected to the action of L-acetyl-carnitine.HCl (40 mg/ml) for 10 or 20 minutes, 30 minutes and 40 minutes. The L-acetyl-carnitine.HCl was then removed and the cells were infected with HSV1 or HSV2 either at this point in time or 24, 48 or 72 hours later.

The viral growth was suppressed completely if the action of L-acetyl-carnitine-HCl took place for at least 20 minutes, even if the infection did not occur until 3 days later.

4. Effect of L-acetyl-carnitine on the viral absorption

The observation that L-acetyl-carnitine is still fully active 4 hours after the infection makes it obvious that it is also active after the initial interaction of the virus with the cell.

Because the pretreatment of the cells with L-acetyl-carnitine inhibits viral growth so successfully, it was investigated whether L-acetyl-carnitine inhibits the adsorption also.

The cells were treated with L-acetyl-carnitine (40 mg/ml) 1 hour before or simultaneously with the infection.

The infection was done with viruses that had been radioactively labelled with tritiated thymidine and the appearance of the label was followed into the cytoplasm and the membrane fraction of the cells as a function of disappearance from the infectious supernatant.

The label was recovered in the membrane and in the cytoplasm fraction of the infected cells in a kinetic pattern, consistent with established data, which indicates the occurrence of viral adsorption and penetration.

5. Stability of L-acetyl-carnitine effect against temperature changes

L-acetyl-carnitine.HCl (40 mg/ml) was subjected to the following treatments:
1. No treatment
2. Standing for 1 week at room temperature
3. 30 minutes at 56° C.
4. 2 hours at 37° C.
5. Seven freezing-thawing cycles.

After these pretreatments, each of the solutions were made to act on cell cultures that had been infected with HSV for 1 hour at 37° C. 24 hours after the beginning of this action, the virus titer was determined in each specimen. All five preparations inhibited the viral growth completely (0 pfu/ml), while the corresponding controls (without L-acetyl-carnitine) exhibited an unimpeded growth of the viruses ($10^7$ pfu/ml).

It can be concluded from this that the antiviral activity of L-acetyl-carnitine is fully stable under the above temperature conditions.

6. Direct effect of L-acetyl-carnitine on viruses

In order to determine the magnitude of the L-acetyl-carnitine effect on the virus itself, i.e., whether the virus itself is attached by the substance and the survival of the latter is not inhibited due to changes in the host cell, tritiated HSV viruses were subjected to the action of L-acetyl-carnitine.HCl (40 mg/ml) or a control without active substance for 1 hour at 37° C. in a test tube without cells. The viruses were then vacuum filtered through a millipore filter (0.22μin pore diameter). The radioactivity remaining on the filter was measured because only the intact viruses are retained on the filter, while the attacked, solubilized viruses, which are broken down into their molecular constituents, are drawn through the filter.

After the viruses are treated with the control preparation, the total original radioactivity is retained on the filter. After treatment with L-acetyl-carnitine, radioactivity measured was only 50% of that originally measured. It can be concluded from this that the direct, structurally damaging action of L-acetyl-carnitine on the virus itself is not insignificant.

7. Effect of L-acetyl-carnitine on herpetic skin lesions

These studies are for determining the effect of L-acetyl-carnitine treatment on the development of classic herpetic diseases on the mouse.

Dilutions of L-acetyl-carnitine.HCl in a polyethylene glycol (PEG) carrier were prepared. This yielded an effective gel for topical application. The L-acetyl-carnitine doses in the gel were 0.5 or 1, 2 and 4 g/ml.

The mice were treated with gels containing L-acetyl-carnitine by local application on the ear $-2$, 0 and $+2$ hours after infection with HSV1 or HSV2 by subcutaneous injection into the treated ear.

The controls consisted of mice treated with PEG without L-acetyl-carnitine and infected in the an analogous manner.

An additional treatment was administered 24 hours later by similar application of the corresponding gel.

All the untreated mice and those treated with 500 mg/ml developed HSV lesions 3 days later (10/10–100%), while none of the mice treated with the 4 g/ml ointment developed a disease during an 8-day period after the infection (0/10–0%).

One-third (33%) of the animals treated with the 1 g/ml of L-acetyl-carnitine ointment and one-fifth of those treated with the 2 g/ml ointment presented minimal symptoms of disease 6 days after the infection.

The others remained free of disease during the entire 8 days.

The ears were removed and the virus titers were determined at the end of the study (8 days).

The virus titers in the ears of the control group were in the range between 1 and $4\times10^4$ pfu/ml.

The two animals that were treated with 1 or 2 g/ml of L-acetyl-carnitine ointment and which exhibited minimal pathological manifestations had titers of 1 and $5\times10^3$ pfu/ml.

The other six animals without disease symptoms, which were treated with 1 and 2 g/ml of L-acetyl-carnitine ointment, presented titers of $1$–$3\times10^2$ pfu/ml.

There were no viruses (0 pfu/ml) in the animals that were treated with 4 g/ml of ointment.

8. Toxicity

L-acetyl-carnitine.HCl has an acute toxicity $LD_{50}$ for mice of more than 3000 mg/kg with intramuscular administration, more than 3600 mg/kg with interperitoneal administration, more than 1600 mg/kg with intravenous administration and more than 18,000 mg/kg with peroral administration. For rats these values are more than 3000 mg/k i.m., 2748 mg/kg i.p., 1000 mg/kg i.v. and more than 10,000 mg/kg p.o.

Long-term studies with guinea pigs and rabbits, to which L-acetyl-carnitine was administered for 26 weeks in doses of 250–500 mg/kg/day perorally and in doses of 50 mg/kg/day i.m., revealed no significant changes in weight, blood composition, liver function, or biochemical values of the blood and urine. Macro-microscopic examinations of the most important organs did not reveal any pathological change either.

The study on dogs did not reveal any signs of a toxicological nature after the i.m. administration of 75, 150 and 300 mg/kg/day either.

It was also observed that topical application induces vasodilatation. Topical application on the skin of the hand of 12 human volunteers in a concentration of 4 mg/ml revealed that the compound does not burn, sting or smart. However, it did produce a minimal pleasant warming effect, presumably due to vasodilatation.

L-acetyl-carnitine is minimally toxic in tissue cell cultures; in particular, it inhibits the protein synthesis of the cells above a concentration of 40 mg/ml.

However, there was no visible toxicity in the topically treated mouse, with the exception of a somewhat reddish local coloration, which was observed with a dose of 4 g/ml and can presumably also be attributed to vasodilatation.

In sum, the data show that L-acetyl-carnitine inhibits the growth of all the viruses examined both in tissue cultures and in the animals. Specifically, the treatment apparently renders the cells refractory to infection and thus appears to deprive all viruses of the ability to survive and propagate. The action that it exerts on infections with HIV could not yet be studied directly because this virus is very difficult to culture in cell types. The trial must thus be carried out directly on humans.

Based on experience with all other quite divergent virus types, it is however expected that the remedy will also prevent the entrance of HIV into the body cells provided the HIV transfer takes place by direct contact, e.g., during sexual intercourse. It is proposed to use the active substance primarily for topical application in a cream carrier, the formulation of which is generally known.

In the above studies the active substance in solution was used in a commercially available cell growth medium well known to professionals, namely "Eagel's MEM" (MEM=minimum essential medium), possibly with the addition of 1% calf-fetus serum.

L-acetyl-carnitine.HCl is soluble in water and the usual solvents in cosmetics. The aqueous solution exhibits an increasing viscosity with increasing concentration. Thus, a solution of 4 g of L-acetyl-carnitine in 1 ml of water is already very strongly viscous.

Two types of creams can be preferably considered, which can be produced in the usual manner:

EXAMPLE 1

Cream for external use for the treatment of herpetic lesions, for example, which can occur after the action of sunlight, UV light or fever.

The carrier contains 15% ethyl alcohol, 2% carboxypolymethylene, 0.1% EDTA and 0.0075% essence of lavender. 10 mg–4 g/ml of L-acetyl-carnitine.HCl is added to this carrier.

The fragrance of the preparation can be modified at will with any available perfume, such as vanilla, jasmine, strawberry, musk, etc.

When applied to the diseased area, a complete recovery results after only 2 days, while ordinary remedies require about 10 days. The ointment also effects a reliable protection on all skin areas smeared with it prior to infection.

The use of the preparation in liquid or semi-liquid form is similar to that with a sun screen. The area to be treated is covered completely and uniformly with a thin layer of the preparation.

EXAMPLE 2

The second ointment type that is proposed for use is produced with or without the addition of a spermicide in an inert carrier gel of a known type for intravaginal use as a potential contraceptive antiviral preparation.

The use of such preparations immediately prior to sexual intercourse and once thereafter is the most expedient procedure.

The ointments can also be used on other parts of the body, such as the anus during anal sexual intercourse.

EXAMPLE 3

Vaginal Cream

| | |
|---|---|
| Sorbitol monostearate | 2% |
| Polysorbitol 60 | 1.5% |
| Spermoid | 2-3% |
| Cetyl stearyl alcohol | 10% |
| 2,8-Octyl dodecanol | 13.5% |
| Benzyl alcohol | 1% |
| L-acetyl-carnitine.HCl | 1-20% |
| Remainder | water |

Instead of ointments, the active substance can also be used in other preferably topically active forms, e.g., as a lotion, suppositories, spray, vaginal capsules or suppositories, etc.

EXAMPLE 4

Anal cream

| | |
|---|---|
| Methyl-p-hydrobenzoate | 7% |
| Propyl-p-hydrobenzoate | 3% |
| L-acetyl-carnitine.HCl | 1-20% |
| Mixtures of polyethylene glycol 400 and polyethylene glycol 4000 in a ratio of 2:1 | remainder |

EXAMPLE 5

Vaginal suppository

| | |
|---|---|
| Benzoic acid | 0.5 g |
| Glyceryl monoricinoleate | 0.2 g |
| Semisynthetic glycerides | 2.35 g |
| L-acetyl-carnitine.HCl | 10 mg to 4 g |

Applications in other pharmaceutical dosage forms, e.g., perorally, intraperitoneally, intramuscularly or intravenously, are currently being tested. Trial series for combatting viral infections in animals and plants are also in progress.

We claim:

1. A process for treating or preventing viral infections in cases involving herpes simplex virus types I and II, cytomegalovirus, adenovirus, varicella-zoster virus, respiratory syncytial virus, polio virus, coxsackie virus, enterovirus, or vaccinia virus in human cells comprising topically treating a quantity of human cells with an amount of L-acetyl-carnitine effective to treat or to prevent viral infections in said human cells.

2. The process according to claim 11 wherein said L-acetyl-carnitine is first admixed with a carrier in the amount of 10 mg, to 4 g, L-acetyl-carnitine per ml, or per g, of carrier.

3. The process according to claim 2 wherein said L-acetyl-carnitine is first admixed with a carrier in the amount of 10 mg, to 4 g, L-acetyl-carnitine per ml, or per g, of carrier and the resultant admixed L-acetyl-carnitine and carrier is then further prepared in the form of a topical preparation selected from the group consisting of an ointment, a lotion, a spray, a vaginal suppository, a vaginal capsule and a suppository.

4. The process according to claim 3 wherein said topical preparation includes about 0.5 g, benzoic acid, about 0.2 g, glyceryl monoricinoleate, about 2.35 g semisynthetic glycerides and between 10 mg, and 4 g, L-acetyl-carnitine.

* * * * *